United States Patent
Henning (10) Patent No.: US 10,799,205 B2
(45) Date of Patent: Oct. 13, 2020

(54) METHOD AND SYSTEM FOR DETERMINING A TRIGGER SIGNAL

(71) Applicant: Siemens Healthcare GmbH, Erlangen (DE)

(72) Inventor: Andre Henning, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 586 days.

(21) Appl. No.: 15/239,867

(22) Filed: Aug. 18, 2016

(65) Prior Publication Data

US 2017/0055934 A1   Mar. 2, 2017

(30) Foreign Application Priority Data

Aug. 24, 2015  (DE) .......................... 10 2015 216 115

(51) Int. Cl.
*A61B 6/00* (2006.01)
*A61B 6/03* (2006.01)
(Continued)

(52) U.S. Cl.
CPC ............ *A61B 6/541* (2013.01); *A61B 5/0077* (2013.01); *A61B 5/7289* (2013.01); *A61B 6/032* (2013.01); *A61B 5/055* (2013.01); *A61B 6/503* (2013.01)

(58) Field of Classification Search
CPC ....... A61B 6/541; A61B 5/7289; A61B 6/032; A61B 5/0077; A61B 6/503; A61B 5/055
See application file for complete search history.

(56) References Cited

U.S. PATENT DOCUMENTS

2005/0036034 A1\* 2/2005 Rea .................... H04N 1/00281
348/207.1
2005/0265585 A1   12/2005 Rowe
(Continued)

FOREIGN PATENT DOCUMENTS

CN         1063624 C    3/2001
CN       102341828 A    2/2012
(Continued)

OTHER PUBLICATIONS

Desjardins et al., "ECG-Gated Cardiac CT,", Apr. 2004, American Journal of Roentgenology, vol. 182, No. 4, pp. 993-1010 (Year: 2004).\*

(Continued)

*Primary Examiner* — Hien N Nguyen
(74) *Attorney, Agent, or Firm* — Harness, Dickey & Pierce, P.L.C.

(57) ABSTRACT

A method for determining a trigger signal for an imaging device is based on receiving a film of a surface of a first body part of a patient. In an embodiment, image values in a region in the images of the film are averaged. The noise of the image values in the region is reduced by way of the averaging. The film is transformed into a temporal signal series on the basis of the averaging. The transformation takes place in such a manner that the temporal series is a measure of the timing pattern of the blood circulation in the area. Furthermore, the temporal signal series is analyzed to ascertain whether the temporal signal series satisfies a preset criterion. Finally, a trigger signal is determined for an imaging device if the temporal signal series satisfies the preset criterion.

20 Claims, 2 Drawing Sheets

(51) Int. Cl.
*A61B 5/00* (2006.01)
*A61B 5/055* (2006.01)

(56) References Cited

U.S. PATENT DOCUMENTS

| | | | |
|---|---|---|---|
| 2010/0309349 A1* | 12/2010 | Kozlowski | H01L 27/14621 348/273 |
| 2011/0251493 A1 | 10/2011 | Poh | |
| 2011/0311119 A1 | 12/2011 | Jeanne et al. | |
| 2013/0245456 A1 | 9/2013 | Ferguson, Jr. | |
| 2013/0317336 A1* | 11/2013 | Zhang | A61B 5/7289 600/407 |
| 2013/0345568 A1 | 12/2013 | Mestha | |
| 2014/0012142 A1 | 1/2014 | Mestha | |
| 2014/0062481 A1 | 3/2014 | Greiser et al. | |
| 2014/0078338 A1* | 3/2014 | Hatano | H04N 9/045 348/222.1 |
| 2015/0042677 A1 | 2/2015 | Shimamura | |
| 2015/0223703 A1 | 8/2015 | Abd-Elmoniem et al. | |
| 2016/0112681 A1* | 4/2016 | Kaestle | A61B 5/11 348/78 |
| 2016/0361043 A1* | 12/2016 | Kim | A61B 8/463 |

FOREIGN PATENT DOCUMENTS

| | | |
|---|---|---|
| CN | 102982317 A | 3/2013 |
| CN | 103654781 A | 3/2014 |
| CN | 104023625 A | 9/2014 |
| EP | 2979631 A1 | 2/2016 |
| WO | WO 2013/036831 | 3/2014 |
| WO | WO 2014155750 A1 | 10/2014 |

OTHER PUBLICATIONS

Poh et al., "Non-contact, automated cardiac pulse measurements using video imaging and blind source separation," May 10, 2010, Optics Express, vol. 18, No. 10, pp. 10762-10774 (Year: 2010).*
Sun et al., "Motion-compensated noncontact imaging photoplethysmography to monitor cardiorespiratory status during exercise," Jul. 2011, Journal of Biomedical Optics, vol. 16, No. 7, pp. 077010-1-077010-9 (Year: 2011).*
Spicher et al. "Eulerian Video Magnification for Heart Pulse Measurements in MRI Scanners," 2012, ACM Transactions on Graphics, vol. 31, No. 4, pp. 4824 (Year: 2012).*
Wu et al. "Eulerian Video Magnification for Revealing Subtle Changes in the World," Jul. 2012, ACM Transactions on Graphics, vol. 31, No. 4, article 65, pp. 65-1-65-8 (Year: 2012).*
Liu et al., "Non-contact heart rate and heart rate variability measurements," Aug. 28-Sep. 1 2012, Proc. of 34th Annual International Conference of the IEEE EMBS, San Diego, California, USA, pp. 2088-2091 (Year: 2012).*
Lempe et al., "ROI Selection for Remote Photoplethysmography," 2013, In Bildverarbeitung für die Medizin, pp. 99-103. Springer (Year: 2013).*
Balakrishnan et al., "Detecting Pulse from Head Motions in Video," Jun. 23-28, 2013, In Proceedings of 2013 IEEE Conference on Computer Vision and Pattern Recognition, Portland, Oregon, USA, pp. 3430-3437 (Year: 2013).*
McLeod et al. "Motion Magnification for Endoscopic Surgery," 2014, Proc. of SPIE Medical Imaging 2014: Image-Guided Procedures, Robotic Interventions, and Modeling, vol. 9036, San Diego, California, USA, pp. 90360C-1-90360C-8 (Year: 2014).*
Kranjec et al., "Non-contact heart rate and heart rate variability measurements: A review," 2014, Biomedical Signal Processing and Control, vol. 13, pp. 102-112 (Year: 2014).*
Krishnamurthy et al., "Tools for cardiovascular magnetic resonance imaging" 2014, Cardiovascular Diagnosis and Therapy, vol. 4, No. 2, pp. 104-125 (Year: 2014).*
Spicher et al. ("In vivo 7T MR imaging triggered by phase information obtained from video signals of the human skin," May 30-Jun. 5, 2015, in Proceedings of the 23nd Annual Meeting of the ISMRM, Toronto, Ontario, Canada, p. 2548 (Year: 2015).*
Spicher et al. "Heart rate monitoring in ultra-high-field MRI using frequency information obtained from video signals of the human skin compared to electrocardiography and pulse oximetry," 2015, Published Online Sep. 12, 2015, Current Directions in Biomedical Engineering, vol. 1, No. 1, pp. 69-72 (Year: 2015).*
Maclaren et al., "Contact-Free Physiological Monitoring Using a Markerless Optical System," 2015, Magnetic Resonance in Medicine, vol. 74, pp. 571-577 (Year: 2015).*
Krug Johannes W. et al: "Optical ballistocardiography for gating and patient monitoring during MRI: an initial study"; In: Compuing in Cardiology 2014; 41; pp. 953-956; ISSN 2325-8861; 2014.
Office Action for Chinese Patent Application No. 201610712715.9 dated Mar. 11, 2019 and English translation thereof.
Chinese Office Action and English translation thereof dated Jun. 28, 2018.
Office Action for Chinese Patent Application No. 201610712715.9 dated Jun. 20, 2019 and English translation thereof.
Office Action for Chinese Patent Application No. 201610712715.9 dated Apr. 28, 2020 and English translation thereof.

* cited by examiner

METHOD AND SYSTEM FOR DETERMINING A TRIGGER SIGNAL

PRIORITY STATEMENT

The present application hereby claims priority under 35 U.S.C. § 119 to German patent application number DE 102015216115.3 filed Aug. 24, 2015, the entire contents of which are hereby incorporated herein by reference.

FIELD

At least one embodiment of the invention generally relates to a method and/or system for determining a trigger signal for an imaging device.

BACKGROUND

The acquisition of image data from an acquisition area of a patient can be matched to a regular movement of the patient. In this situation the acquisition typically takes place depending on the movement of the heart of the patient. In particular, in the case of three-dimensional imaging methods such as computed tomography it is desirable to match the acquisition of image data to the movement of the heart in order to achieve a high spatial and temporal resolution. If an acquisition of image data via X-ray radiation is matched to the movement of the heart, then as small a dose as possible can be applied.

The acquisition of image data from an acquisition area resides in the acquisition of a raw data series. Such raw data can for example be obtained while the gantry of a computed tomography system is rotating. The raw data in question can in particular be a series of individual projections of an acquisition area, where the acquisition area is penetrated by X-ray radiation. The raw data is then a measure of the attenuation of the X-ray radiation by the acquisition area. Matching of the acquisition of image data to the movement of the heart typically takes place by effecting the commencement of the acquisition of a raw data series depending on the movement of the heart.

According to known systems, the movement of the heart is characterized by an electrocardiogram, ECG for short, which is determined via sensors galvanically coupled to the patient. The matching of the acquisition of image data to the ECG of the patient is also known as ECG triggering. A conventional ECG triggering is however time-consuming and error-prone. Preparations are thus required for affixing the sensors, for example if it is necessary to shave the contact surface of the patient fitted with the sensors. Furthermore, the cooperation of the patient is required in order to affix the sensors quickly and reliably. Errors can be caused in particular by the impedance of the skin of the patient changing during the acquisition of the ECG. Imprecisely or unevenly affixed sensors may also distort the ECG.

SUMMARY

Against this background, the inventor has discovered that it is desirable to quickly and reliably determine a trigger signal for an imaging device. The trigger signal should be determined depending on the movement of the heart of the patient in this situation.

At least one embodiment is directed to a method, a system, a computer program product and/or a computer readable medium.

Embodiments of the invention in relation to the claimed devices and also in relation to the claimed method are described in the following. Features, advantages or alternative embodiments mentioned here can likewise also be transferred to the other claimed subject matters and vice versa. In other words, the objective claims (which for example are directed at a device) can also be developed with the features which are described or claimed in conjunction with a method. The corresponding functional features of the method are embodied here by corresponding objective modules.

The inventor has recognized that the coloration of a skin region of a patient changes depending on the movement of the heart. As a result of the inflow and outflow of blood into and out of a skin region during the cardiac cycle the skin can in particular assume higher and lower brightness values and/or color values.

At least one embodiment of the invention relates to a method for determining a trigger signal for an imaging device, comprising:
  receiving a film of a surface of a first body part of a patient, wherein the film comprises a plurality of images,
  averaging image values in a region in the images of the film, wherein the region localizes a particular area of the body part,
  transforming the film into a temporal signal series on the basis of the averaging, wherein the temporal signal series is a measure of the timing pattern of the blood circulation in the area,
  analyzing the temporal signal series to ascertain whether the temporal signal series satisfies a preset criterion, and
  determining a trigger signal for an imaging device if the temporal signal series satisfies the preset criterion.

At least one embodiment of the invention furthermore relates to a system for determining a trigger signal, comprising:
  interface for receiving a film of a surface of a first body part of a patient, wherein the film comprises a plurality of images,
  computing unit including a processor, wherein the processor is programmed to perform at least:
    averaging image values in a region in the images of the film, wherein the region localizes a particular area of the body part,
    transforming the film into a temporal signal series on the basis of the averaging, wherein the temporal signal series is a measure of the timing pattern of the blood circulation in the area,
    analyzing the temporal signal series to ascertain whether the temporal signal series satisfies a preset criterion, and
    determining a trigger signal for an imaging device if the temporal signal series satisfies the preset criterion.

At least one embodiment of the invention also relates to a computer program product having a computer program and a computer readable medium. A largely software-based implementation has the advantage that systems or computing units also already used hitherto can be field-upgraded in a simple manner via a software update in order to function in the manner according to at least one embodiment of the invention. Where applicable, in addition to the computer program such a computer program product can comprise additional elements such as for example documentation and/or additional components including hardware components such as for example hardware keys (dongles etc.) for using the software.

BRIEF DESCRIPTION OF THE DRAWINGS

The invention will be described and explained in detail in the following with reference to the example embodiments illustrated in the figures.

In the drawings

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/Digital Video Disc (DVD)/Compact Disc (CD)-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the proposed method for determining a trigger signal for an imaging device is therefore based on receiving a film of a surface of a first body part of a patient. In this situation the film comprises a plurality of images. The film can be received via an interface. Then follow a number of image processing steps which can be performed by a computing unit having an appropriately programmed processor.

In at least one embodiment of the process, image values in a region in the images of the film are averaged, where the region localizes a particular area of the body part. The noise of the image values in the region is reduced by way of the averaging. The film is transformed into a temporal signal series on the basis of the averaging, where the temporal signal series is a measure of the timing pattern of the blood circulation in the area. Furthermore, the temporal signal series is analyzed to ascertain whether the temporal signal series satisfies a preset criterion. Finally, a trigger signal is determined for an imaging device if the temporal signal series satisfies the preset criterion.

At least one embodiment of the proposed method is based on image processing steps which can be performed quickly and reliably by way of modern computing units. In particular, the processing of individual images can take place in a period of time which is orders of magnitude less than the period of time of a cardiac cycle of the human heart. The trigger signal can thereby be defined so quickly that the trigger signal is suitable for triggering a subsequent acquisition of image data by an imaging device, in particular for the acquisition of image data of the human heart during a diastolic or systolic phase. Furthermore, the reliability achieved when determining a trigger signal is increased compared with the prior art because the error-prone contacting of sensors is dispensed with.

According to an embodiment of the invention, the film is based on the detection of light in the visible spectral range. The film can therefore also be recorded by using an optical camera. Furthermore, the film can be recorded under the influence of a broadband light source; in particular the broadband light source is able to continuously emit light in the entire visible spectral range. Such a broadband light source is for example given by known ceiling lighting in the form of an Light Emitting Diode (LED) lamp or by sunlight. With regard to this embodiment, the invention is distinguished in particular from methods which are based on the detection of light in the infrared or UV range. The film can furthermore be based on the detection of light reflected by the surface. The invention is then also distinguished from methods which are based on the screening of a body part and the absorption of electromagnetic radiation associated therewith. Furthermore, the film can be recorded without the influence of a narrowband light source. In the case of a narrowband light source, the frequency bandwidth of the spectrum is substantially smaller than the frequencies of the emitted light. A narrowband light source can in particular be embodied in the form of a laser.

The camera can be installed locationally fixed in order to thereby facilitate reliable recording of the film. The camera can in particular be installed on the ceiling or the wall of a room or on an imaging device. The camera can be embodied both in order to record a color film and also in order to record a grayscale film. The camera in question can for example be a Charge Coupled Device (CCD) camera or a Complementary Metal-Oxide Semiconductor (cMOS) camera.

The images of the film can be embodied in different variants of the invention as 2D images or as 3D images. A 2D image has a grid of image elements, where one or more image values are assigned to each image element. In the case of a 3D image, depth measurement data is also assigned to the image elements in addition to the image values. The depth measurement data thus represents information in a third spatial dimension. The camera in question can therefore also be a 3D camera which is suitable for recording 3D images. A 3D camera is embodied for example as a stereo camera or as a time-of-flight camera. The 3D camera can also be designed to record a 3D image via structured illumination.

Furthermore, the timing interval between the images of the film is typically constant. The image processing according to an embodiment of the invention is thereby facilitated. According to a further embodiment of the invention, the film has a frequency of at least 50 Hz, in particular of at least 100 Hz. The transformation into the temporal signal series takes place particularly reliably as a result of the high frequency. The sampling at a frequency of 50 Hz or 100 Hz is furthermore fast in comparison with the human cardiac cycle and thereby enables the trigger signal to be determined particularly precisely.

According to a further embodiment of the invention, the region localizes the same area of the body part in each of the images. The area in question is a skin region. This means that the temporal signal series is based on a change in the blood circulation in the same area and is thereby particularly reliable.

According to a further embodiment, the images are registered with one another, wherein a movement of the body part of the patient is compensated for. The registration in question is for example an elastic or a rigid registration. One image from the film can be selected here as a reference image. Furthermore, the registration can take place in landmark based fashion. In this case landmarks are sought in each of the images and the images are registered with one another in such a manner that the landmarks are brought into alignment. In particular, the body part in question can be the face of a patient where distinctive points of the face, in particular eyes or eyebrows, are used as landmarks. Furthermore, the registration can take place in such a manner that the region has the same image coordinates in each image.

According to a further embodiment of the invention, the averaging is based on a segmentation of the region in the images. Such a segmentation preferably takes place at least partially automatically. As a result of the segmentation the region can be determined particularly quickly and reliably in such a manner that the region localizes the same area of the body part in each of the images. A region-oriented segmentation algorithm or an edge-based segmentation algorithm for example is used for the segmentation. Furthermore, the segmentation can take place fully automatically.

In the context of the present application "automatically" means that the respective step is performed independently by a computing unit and essentially no interaction by an operator is required for the respective step. The operator must at most confirm computed results or perform intermediate steps. For example, the operator can set a seed point for the segmentation. In further variants of the invention having steps performed "fully automatically" no interaction whatsoever by an operator is required in order to perform the steps. In particular, all the steps of the claimed method can be performed "fully automatically". Regardless of whether the individual steps are performed "automatically" or "fully automatically", the method according to an embodiment of the invention can be part of a work process which additionally requires interaction by an operator. The interaction by the operator can include the operator manually selecting an imaging protocol and/or a clinical question, for example from a menu presented via a screen.

According to a further embodiment of the invention, the temporal signal series is embodied unidimensionally. The film is therefore transformed into the temporal signal series in such a manner that the image values of an image are combined in a single signal value of the signal series. This means that the signal series is particularly low-noise. Furthermore, compared with the original film the signal series has a very low data volume, which means that the data series can be analyzed particularly quickly.

According to a further embodiment of the invention, the image values comprise intensity values and/or color values. If the image values comprise only intensity values, then the invention is particularly simple and cost-effective to implement. In particular, the camera then only needs to be designed to record a grayscale film. If the image values also comprise color values, then the inflow and outflow of blood in the skin region can be determined particularly precisely and reliably. The color values can be based on normal color scales, in particular on a color scale having the color channels red, green and blue or on a color scale having the color channels cyan, magenta and yellow.

According to a further embodiment of the invention, the signal series is analyzed to ascertain whether the temporal signal series exceeds or undershoots a threshold value. For example, the signal series is analyzed to ascertain whether the change in the signal values exceeds or undershoots a preset threshold value. Such a type of analysis is particularly simple to implement and can be carried out very quickly.

According to a further embodiment of the invention, the threshold value is computed depending on the temporal signal series. The threshold value is therefore embodied adaptively and may change during an ongoing temporal signal series. Such a type of analysis makes it possible in particular to determine trigger signals individually for a patient and thereby particularly precisely and reliably.

Furthermore, the signal series can be analyzed by adjusting a function to the temporal signal series. An example of such a function is s polynomial function. By adjusting the function to the signal series it is possible to determine the future development of the signal series and thereby the future cardiac cycle of the patient. Furthermore, the continuous writing of the signal series with a function enables additional mathematical analyses. The signal series can thus be analyzed by differentiating or integrating the adjusted function. As a result of differentiation of the function the change in the blood flow in the skin region can be determined particularly precisely. The cardiac cycle of the patient and also the trigger signal can thereby also be determined particularly precisely.

At least one embodiment of the invention furthermore relates to a system for determining a trigger signal, comprising an interface for receiving a film of a surface of a first body part of a patient and also a computing unit having a processor. In at least one embodiment, the system is embodied in order to carry out at least one embodiment of the method described above and the embodiments thereof in that the interface and the computing unit are embodied in order to perform the corresponding method steps. In at least one embodiment, the processor can be programmed to perform steps of at least one embodiment of the described method.

At least one embodiment of the invention also relates to a computer program product having a computer program and a computer readable medium. A largely software-based implementation has the advantage that systems or computing units also already used hitherto can be field-upgraded in a simple manner via a software update in order to function in the manner according to at least one embodiment of the invention. Where applicable, in addition to the computer program such a computer program product can comprise additional elements such as for example documentation and/or additional components including hardware components such as for example hardware keys (dongles etc.) for using the software.

Figure 1:
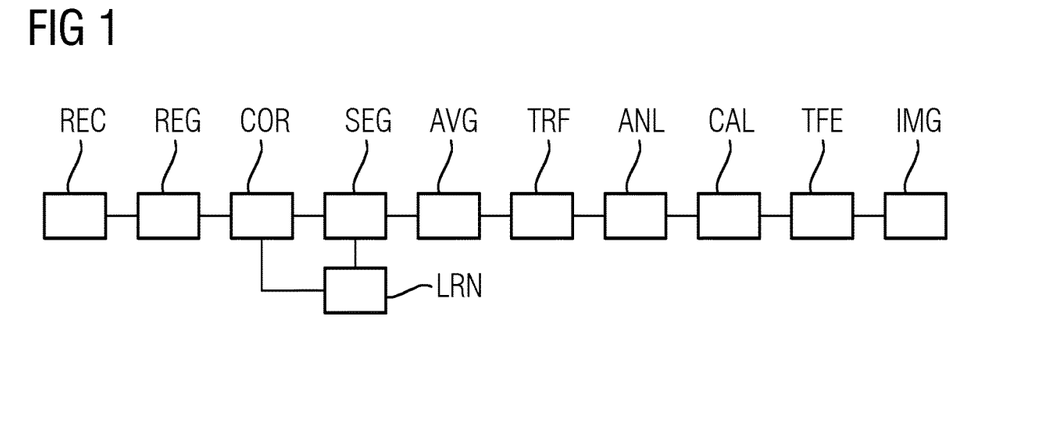
FIG. 1 shows a flowchart of a method for determining a trigger signal.

FIG. 1 shows a flowchart of a method for determining a trigger signal. The example embodiment shown here is based on a film of the face of a patient 3. The film has been recorded at a frequency of 100 Hz. In alternative example embodiments of the invention the frequency can be lower or higher. Preferably however the film is recorded at a frequency of at least 50 Hz in order to thus obtain a low-noise temporal signal series 22. The film is received by an interface 16 of a system for determining a trigger signal. The system comprises a computing unit 15 having a processor, wherein the processor is programmed in order to perform a plurality of image processing steps and thereby to compute the trigger signal.

In the example embodiment shown here the images 19 of the film are registered with one another after being received REC. The registration REG ensures that the movement of the face of the patient 3 is compensated for. In this situation the first image 19 of the film can be selected as a reference image with which the other images 19 of the film are registered. Furthermore, landmarks 21 are recognized in a first image 19 of the face, in particular the eyes, the eyebrows, the mouth and the nose. The registration REG then takes place on the basis of the landmarks 21. To this end the landmarks 21 must also be recognized in the following images 19. The images 19 can then be registered with the first image 19 by superimposing the landmarks 21 on one another. Alternative methods can also be used for the registration REG; for example, the images 19 can be registered with the first image 19 by way of a correlation with one another. In this case the positions of the landmarks 21 within the images 19 can also be correlated with one another.

Furthermore, systematic differences between the images 19 can be compensated for in a correction step COR. For example, a systematic difference can arise as a result of a change in illumination during recording of the film. To this end, the summed intensity values of an entire image 19 can be compared with the summed intensity values of other images. The intensity values of an image 19 can now be normalized depending on the comparison. The intensity values of an image 19 can also be normalized depending on the intensity distribution in the image 19. Furthermore, the images 19 can also be filtered and noise-reduced in the correction step COR, for example via a Gaussian filter.

In the example embodiment shown here the segmentation SEG of a region 20 takes place on the basis of a learning algorithm. In this case the computing unit 15 or a computer program learns how a region 20 is segmented within the images 19. In this situation the region 20 should localize the same area of the body part in each image 19. The process of learning LRN with a learning algorithm can take place separately from the processing of the film on the basis whereof a trigger signal is to be determined. The process of learning LRN then takes place on the basis of other films before the method for determining a trigger signal is carried out. The learning LRN can be based on films of a person other than the patient 3. Furthermore, the learning LRN can be based on films of a particular body part of a plurality of test persons. A learning algorithm based on films of a particular body part of a plurality of test persons is also referred to as a population-averaged learning algorithm. Accordingly, the segmentation SEG can be based on a population-averaged learning algorithm.

Learning LRN includes a model establishing a functional relationship between training values. Such a model can be embodied as a software module and thereby be an element of a computer program or of a computing unit 15. When the trained model receives an input value, for example an information item relating to the edges of a region 20 or information items relating to landmarks 21, then it outputs a corresponding function value, for example a segmented region 20. The learning LRN in question can be both supervised learning and also unsupervised learning or reinforcement learning. With supervised learning, the function value is preset for a particular input value. Examples of supervised learning are automatic classification or artificial neural networks. With unsupervised learning, the model comprises one or more rules which independently relate the training values to one another, for example via categorization. Examples of unsupervised learning are so-called EM algorithms (expectation maximization algorithm).

Furthermore, the learning can take place both in the spatial domain of the images 19 of the film and also in the frequency domain. If a Fourier transform is applied to the image values arranged in the form of a grid of the images 19, then the image values are available in the frequency domain. In this situation the Fourier transform can be applied both to intensity values and also to color values. In particular, Fourier transforms can be applied separately to the proportions the intensity values and also the color values.

The image values in the regions 20 are then collected and further processed. In particular, an averaging AVG of the image values takes place. During averaging AVG an average value is computed which is a measure of the blood circulation in the area. The average value also satisfies the function of a signal value of the signal series 22. During the averaging the information content of the image values is reduced. The averaging comprises for example the computation of an arithmetic mean, a geometric mean, a harmonic mean, a quadratic mean or also a median. The averaging AVG of the image values can take place separately for the intensity values and for the color values. For example, a first average value is defined on the basis of the intensity values of the image elements in the region 20 and further average values are defined separately on the basis of the color values of the image elements. In particular, in this situation an average value can be determined in each case for the color channels red, green and blue. Accordingly, the temporal signal series 22 can also be embodied multidimensionally. For example, the signal series 22 comprises a temporal sequence of averaged intensity values and also of averaged color values. In particular, the temporal signal series cannot contain any spatial image information and nevertheless be embodied multidimensionally.

The transformation TRF of the film into a temporal signal series 22 then takes place on the basis of the averaging, wherein the temporal signal series 22 is a measure of the timing pattern of the blood circulation in the area. The transformation takes place in such a manner that the sequence of the average values as signal values in the temporal signal series 22 corresponds to the sequence of the images 19 of the film. Furthermore, the temporal signal series 22 can be output graphically, in particular on a screen 11.

Figure 3:
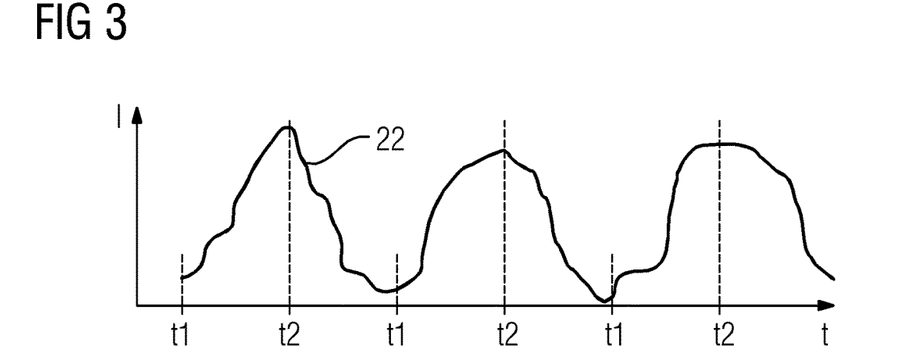
FIG. 3 shows a temporal signal series.

The analysis ANL of the temporal signal series 22 now takes place to ascertain whether the temporal signal series 22 satisfies a preset criterion. The analysis ANL includes deriving an analysis value from the temporal signal series 22, which analysis value does not directly correspond to a signal value. For example, the analysis value can characterize the relationship of different signal values or the progress of the temporal signal series 22 in a particular time window. The change in the signal values, in other words the averaged color values and/or the averaged intensity values, within the signal series 22 can also be analyzed. In particular, the change in the color values of different color channels can be analyzed both absolutely and also relatively with respect to each other. For example, it is possible to analyze how the color values of the red and of the green color channel change relative to each other. Furthermore, both the original signal series 22 and also a mathematical derivation of the function can be analyzed as described in the following. The original signal series 22 is illustrated in FIG. 3.

In the example embodiment of the invention shown here the temporal signal series 22 is analyzed to ascertain whether the temporal signal series 22 or an analysis value derived therefrom exceeds or undershoots a threshold value. The threshold value can already be specified prior to the analysis ANL, or it can be computed depending on the temporal signal series 22. The threshold value can thus be computed depending on an amplitude of the temporal signal series 22. In particular, the threshold value can be computed depending on the average value of the amplitude values or the maximum amplitude value of the temporal signal series 22 within a particular time window. Different threshold values can therefore also be computed for a temporal signal series 22. Furthermore, a third threshold value can also be computed depending on a first threshold value and/or a second threshold value. The third threshold value can in particular be computed as a weighted sum of the second threshold value and the first threshold value.

In further embodiments of the invention the analysis ANL can also include determining amplitude values at the beginning and at the end of the rising edge for rising edges of the temporal signal series 22. Furthermore, the difference between the amplitude values at the beginning and at the end of the rising edge can be correlated, for example the amplitude values can be averaged or subtracted from one another. The time window of the rising edge can also be determined in this context. An average value or the difference between amplitude values and also the time window of the rising edge are in each case an example of an analysis value. Such analysis values can now be computed for a plurality of amplitudes within the temporal signal series 22. It is possible on the basis of the average value or the difference between amplitude values to determine whether a signal value attains a local minimum. The preset criterion can therefore include the signal value attaining a local minimum.

Furthermore, the determination CAL of a trigger signal for an imaging device takes place if the temporal signal series 22 satisfies the preset criterion. For example, the trigger signal can be generated with a preset time delay compared with the point in time at which the criterion is satisfied. In particular, the trigger signal can be determined if no trigger signal has been determined in a preceding period of time, in particular a period of time of 500 milliseconds, 200 milliseconds or 100 milliseconds. The preset time delay can also be dependent on the time window of one or more rising edges. In particular, the preceding period of time can be given by a particular proportion of the average value of the time window of the rising edge. Such a proportion can be 5%, 10%, 15% or 20% in different embodiments of the invention.

Furthermore, in the embodiment shown here the transfer TFE of the trigger signal 22 from the computing unit 15 to the imaging device takes place, where the imaging device is designed in order to acquire IMG image data from an acquisition area of the patient 3 depending on the trigger signal. In this situation the trigger signal can also be transferred over a network 24. Furthermore, the trigger signal can also be transferred over a direct data connection 25.

Figure 2:
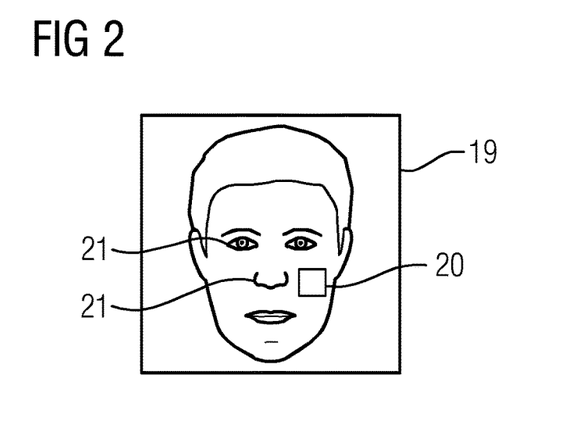
FIG. 2 shows an image of a film.

FIG. 2 shows an image of a film. The face of a patient 3 is shown as a body part in the image 19. An area of the cheek of the patient 3 is segmented as a region 20. The segmentation SEG takes place on the basis of landmarks 21 such as the eyes, the nose or the outer contour of the face of the patient 3. In this situation the region 20 is defined by way of the relative distance thereof from the eyes and/or the nose and/or the outer contour of the face. If the image values in the region 20 are now averaged, then the resulting average value is a measure of the blood circulation in the area of the cheek of the patient 3. If the same area of the cheek of the patient 3 is now segmented as a region 20 in a plurality of images 19 of the film and if the image values in the region 20 are in each case averaged in the same manner, then the resulting average values are a measure of the timing pattern of the blood circulation in the cheek of the patient 3. By averaging AVG the image values, the film is transformed into a temporal signal series 22.

Such a temporal signal series 22 is shown in part in FIG. 3, where the unitless intensity I of the signal values is plotted against the time t. In the example shown here this is a unidimensional signal series 22, in which case both color values and also intensity values have been averaged in order to determine a signal value for each image 19 of the film. The signal series 22 shown is based on a film at 100 Hz which means that the individual signal values are not explicitly illustrated in the representation chosen here. The duration of the part shown here of the signal series 22 is three seconds. The shape of the temporal signal series 22 differs from a conventional ECG. The beginning and the end of the rising edges are identified in FIG. 3 by t1 and t2 respectively.

Figure 4:
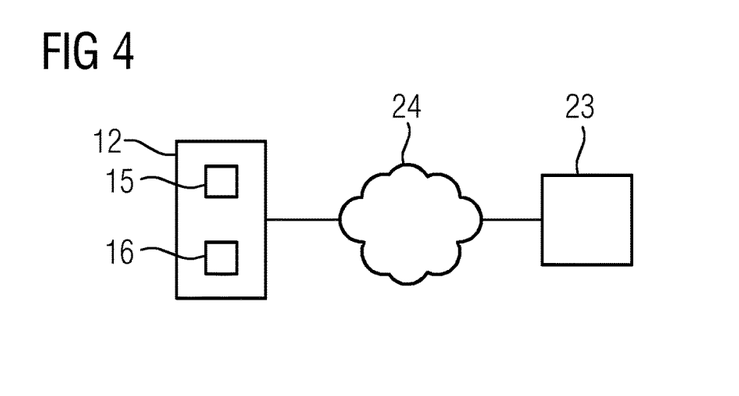
FIG. 4 shows a system for determining a trigger signal.

FIG. 4 shows a system for determining a trigger signal. In the simplest case the system comprises an interface 16 for receiving REC a film and also a computing unit 15 having a processor, wherein the processor is programmed in order to perform at least the following steps:

averaging AVG image values in a region 20 in the images 19 of the film, wherein the region 19 localizes a particular area of the body part, transforming TRF the film into a temporal signal series 22 on the basis of the averaging, wherein the temporal signal series 22 is a measure of the timing pattern of the blood circulation in the area, analyzing ANL the temporal signal series 22 to ascertain whether the temporal signal series 22 satisfies a preset criterion, and determining CAL a trigger signal for an imaging device if the temporal signal series 22 satisfies the preset criterion.

In further embodiments of the invention the processor can also be programmed to perform the other previously described method steps, in particular in image processing. Furthermore, the film can be stored on a server 23 which means that the film can be transferred over a network 24 to a system embodied as a client for determining a trigger signal. A computer program according to an embodiment of the invention is then stored in executable form on the client. Furthermore, the system for determining a trigger signal can be connected to an imaging device in such a manner that the trigger signal can be transferred from the system to the imaging device.

Figure 5:
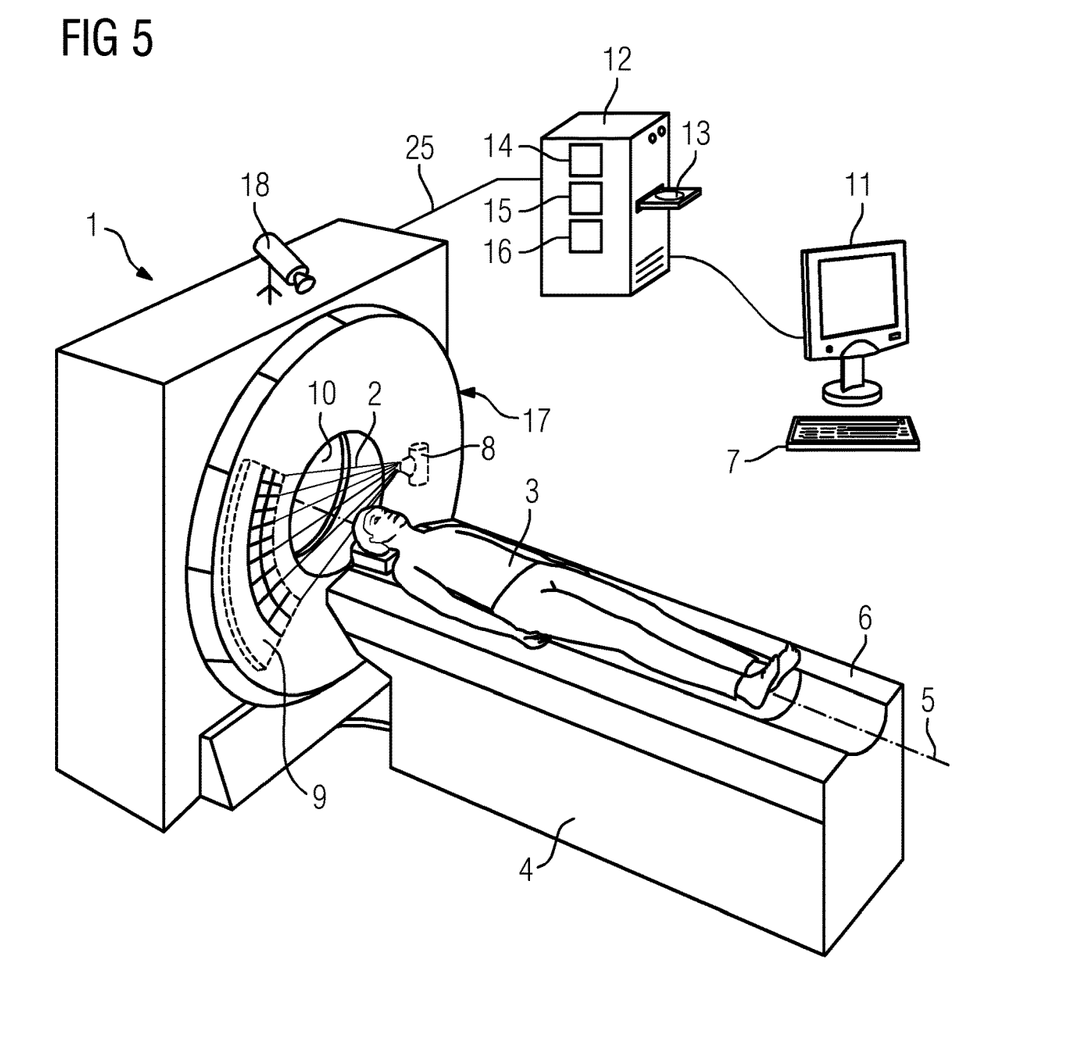
FIG. 5 shows a system for determining a trigger signal having an imaging device.

FIG. 5 shows a system for determining a trigger signal having an imaging device 1. The imaging device 1 in question shown here is a CT device. The computed tomography device shown here has an acquisition unit 17, comprising a radiation source 8 in the form of an X ray source and also a radiation detector 9 in the form of an X ray detector. The acquisition unit 17 rotates about a system axis 5 while projections are acquired, and the X ray source emits beams 2 in the form of X rays during the acquisition. The X ray source in question in the example shown here is an X ray tube. The X ray detector in question in the example shown here is a row detector having a plurality of rows.

In the example shown here, a patient 3 lies on a patient examination table 6 while projections are acquired. The patient examination table 6 is connected to a table pedestal 4 such that it supports the patient examination table 6 carrying the patient 3. The patient examination table 6 is designed in order to transport the patient 3 along a direction of acquisition through the aperture 10 of the acquisition unit 17. The direction of acquisition is given as a general rule by the system axis 5, about which the acquisition unit 17 rotates while X-ray projections are acquired. In the case of a spiral acquisition, the patient examination table 6 is transported continuously through the aperture 10 while the acquisition unit 17 rotates about the patient 3 and acquires X-ray projections. The X-rays thereby describe a spiral on the surface of the patient 3.

Furthermore, the system shown here has a 3D camera 18 which is designed with an interface 16 for receiving REC a film having 3D images acquired via the 3D camera 18. In the example shown here the interface 16 is embodied as part of a computer 12. The interface 16 in question is one of the generally known hardware or software interfaces, for example the PCI bus, USB or FireWire hardware interfaces. The interface 16 can also enable a wireless connection, in particular using WLAN or Bluetooth. The computer 12 is connected to an output unit in the form of a screen 11 and also an input unit 7. The screen 11 is designed in order to display different image information items, in particular on the basis of the film. The input unit 7 can be used in order to start the computer program according to an embodiment of the invention or to select parameters for performing the method according to an embodiment of the invention. The input unit 7 in question is for example a keyboard, a mouse, a so-called touch screen, or also a microphone for voice input.

Furthermore, the computer 12 of the imaging device 1 shown here comprises a reconstruction unit 14 for reconstructing a tomographic image from raw data. The imaging device 1 also has a computing unit 15. The computing unit 15 can interact with a computer readable data medium 13, in particular in order to carry out a method according to an embodiment of the invention via a computer program having program code. Furthermore, the computer program can be stored in retrievable form on the machine readable data medium 13. In particular, the machine readable medium in question can be a CD, DVD, Blu-ray Disc, a memory stick or a hard drive. Both the computing unit 15 and also the reconstruction unit 14 can be embodied in the form of hardware or in the form of software. For example, the reconstruction unit 14 can be embodied as a so-called FPGA (field programmable gate array) or comprise an arithmetic logic unit. The computing unit 15 shown here has a processor. The processor in question can be a microprocessor. The processor can have a plurality of cores.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a trigger signal for an imaging device, comprising:

receiving a series of recorded images of a surface of a first body part of a patient via at least one processor;

segmenting a region of the first body part in the recorded images, wherein the segmenting takes place on a basis of a learning algorithm;

averaging image values, including at least one of intensity values or color values, of blood circulation in the region in the recorded images, the region localizing an area of the first body part, wherein the averaging is based on the segmentation;

transforming the recorded images into a temporal signal series based upon the averaging such that image values of an image are combined in a single signal value of the temporal signal series, the temporal signal series being a measure of a timing pattern of the blood circulation in the area;

analyzing the temporal signal series to ascertain whether the temporal signal series satisfies a preset criterion; and determining a trigger signal of an imaging device based on a change in coloration of a patients skin via a series of recorded images upon the analyzing indicating that the temporal signal series satisfies the preset criterion, and compensating for a change in illumination during recording of the series of recorded images by comparing summed intensity values of an entire image with summed intensity values of other images, and normalizing the intensity values based on the comparison.

2. The method of claim 1, wherein the series of recorded images are recorded at a frequency of at least 50 Hz.

3. The method of claim 1, wherein the region in each of the images localizes the same area of the first body part, and wherein the area is a skin region.

4. The method of claim 1, further comprising:
registering the images with one another, wherein a movement of the first body part of the patient is compensated for.

5. The method claim 1, further comprising:
segmenting the region in the images, wherein the averaging is based on the segmentation.

6. The method of claim 1, wherein the temporal signal series is unidimensional.

7. The method of claim 1, wherein the temporal signal series is analyzed to ascertain whether the temporal signal series exceeds or undershoots a threshold value.

8. The method of claim 7, wherein the threshold value is computed depending on the temporal signal series.

9. The method of claim 1, wherein the analyzing includes forming a mathematical derivation of a function of the temporal signal series.

10. A system for determining a trigger signal for an imaging device, comprising:
at least one processor configured to perform operations including
receiving a series of recorded images of a surface of a first body part of a patient,
segmenting a region in the recorded images, wherein the segmenting takes place on a basis of a learning algorithm,
averaging image values, including at least one of intensity values or color values, in the region in the series of recorded images, the region localizing an area of the first body part, wherein the averaging is based on the segmenting,
transforming the series of recorded images into a temporal signal series based upon the averaging such that image values of an image are combined in a single signal value of the temporal signal series, the temporal signal series being a measure of a timing pattern of a blood circulation in the area,
analyzing the temporal signal series to ascertain whether the temporal signal series satisfies a preset criterion, and
determining a trigger signal of an imaging device based on a change in coloration of a patients skin via a series of recorded images upon the analyzing indicating that the temporal signal series satisfies the preset criterion, and
compensating for a change in illumination during recording of the series of recorded images by comparing summed intensity values of an entire image with summed intensity values of other images, and normalizing the intensity values based on the comparison.

11. The system of claim 10, further comprising:
wherein the system is designed to transfer the trigger signal from the at least one processor to the imaging device, and wherein the imaging device is designed to acquire image data from an acquisition area of the patient depending on the trigger signal.

12. A memory of a system for determining a trigger signal, storing program sections to perform the method of claim 1 when the program sections are executed by the system for determining a trigger signal.

13. A non-transitory computer readable medium, on which program sections which are readable and executable by at least one processor are stored, to perform the method of claim 1 when the program sections are executed by the at least one processor.

14. The method of claim 1, wherein the series of recorded images are recorded at a frequency of at least 100 Hz.

15. The method of claim 2, wherein the region in each of the images localizes the same area of the first body part, and wherein the area is a skin region.

16. The method of claim 2, further comprising:
registering the images with one another, wherein a movement of the first body part of the patient is compensated for.

17. The method of claim 2, wherein the temporal signal series is analyzed to ascertain whether the temporal signal series exceeds or undershoots a threshold value.

18. The method of claim 17, wherein the threshold value is computed depending on the temporal signal series.

19. The system of claim 11, wherein the imaging device is a CT device.

20. The system of claim 11, wherein the imaging device is an MRI device.

* * * * *